Figure 1:
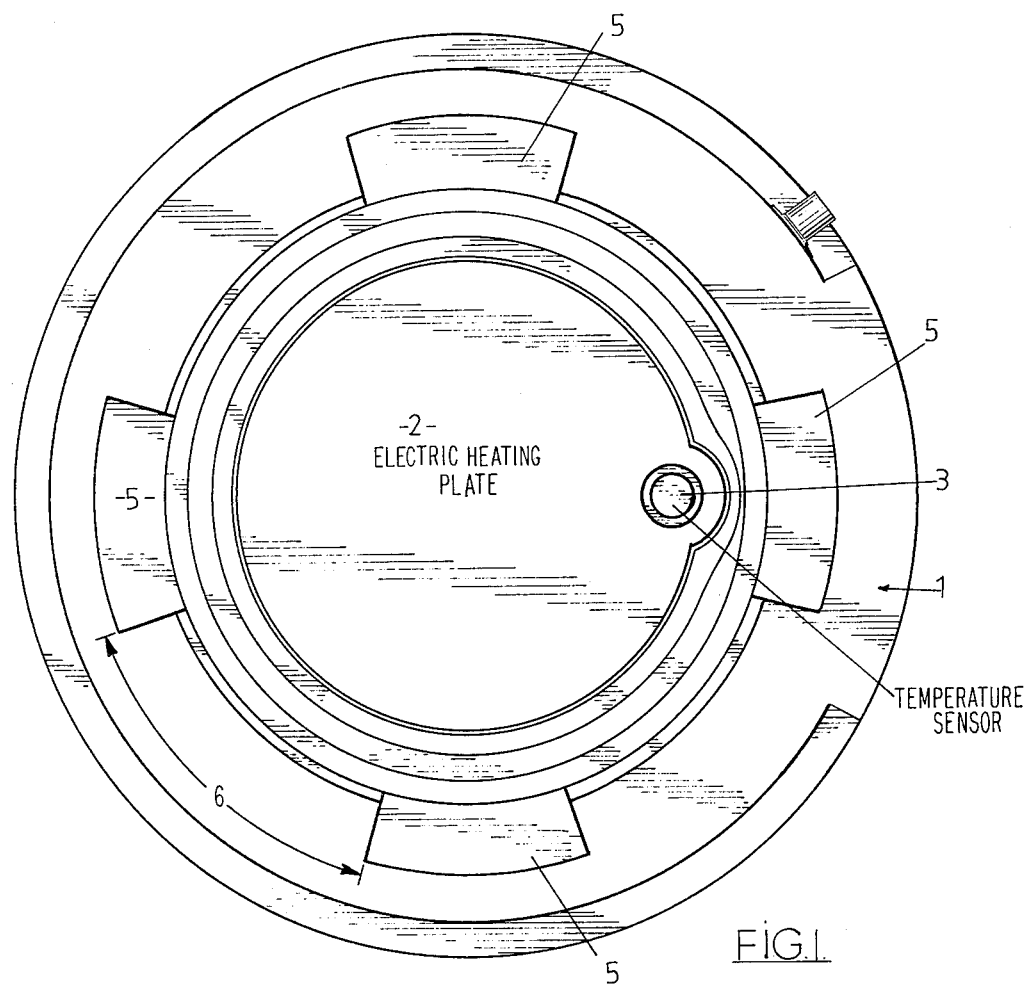

United States Patent [19]

O'Hare et al.

[11] 4,203,027
[45] May 13, 1980

[54] ELECTRICALLY HEATED HUMIDIFYING APPARATUS

[75] Inventors: David H. O'Hare; Christopher G. Brickell; Lindsay G. Spilman, all of Auckland, New Zealand

[73] Assignee: Fisher & Paykel Limited, Auckland, New Zealand

[21] Appl. No.: 862,687

[22] Filed: Dec. 21, 1977

[30] Foreign Application Priority Data

Mar. 7, 1977 [NZ] New Zealand .......................... 183517

[51] Int. Cl.² ...................... H05B 1/00; A61M 15/00
[52] U.S. Cl. .................................... 219/275; 128/192;
128/203.27; 219/311; 219/433; 219/436;
248/154; 248/310; 261/142
[58] Field of Search ................ 219/242, 271, 275–276,
219/429, 432–436, 438, 311, 536; 128/186,
192–194, 212; 220/69, 293; 261/141–142;
126/24, 38, 215, 218; 403/26, 111, 339;
248/154, 310, 311.1, 313

[56] References Cited

U.S. PATENT DOCUMENTS

| 1,083,254 | 12/1913 | Hurley | 248/310 |
| 2,171,664 | 9/1939 | McFarland | 248/154 |
| 2,666,607 | 1/1954 | Hauf | 248/154 |
| 3,659,604 | 5/1972 | Melville et al. | 219/276 X |
| 3,982,095 | 9/1976 | Robinson | 219/273 |

FOREIGN PATENT DOCUMENTS 214709 6/1908 Fed. Rep. of Germany .......... 248/310

Primary Examiner—A. Bartis
Attorney, Agent, or Firm—Holman & Stern

[57] ABSTRACT

An electrically heated humidifying apparatus includes a humidifier element detachably secured to a humidifier heater with the base of the humidifier element in engagement with the electric heating plate of the humidifier heater. The humidifier element is secured to the humidifier heater by an intermediate adaptor having a ring portion with spaced lugs interfitting with correspondingly spaced lugs on the humidifier heater and a horse-shoe shaped portion adapted to slidably receive the humidifier element and engage with an annular shoulder on the humidifier element.

2 Claims, 8 Drawing Figures

ELECTRICALLY HEATED HUMIDIFYING APPARATUS

This invention relates to humidifying apparatus.

It is an object of the present invention to provide humidifying apparatus which will at least provide the public with a useful choice.

Accordingly in one aspect the invention consists in an intermediate adaptor having (1) a humidifier heater connector which in use is attached to a humidifier heater having a heating surface and (2) a humidifier element connector which in use is connected to a humidifier element having a surface for heating. When both connections are made said surface for heating is maintained in a heating disposition relative to said heating surface.

In a further aspect, the invention consists in the combination of a humidifier heater having a heating surface and a holding means comprising circumferentially spaced heater lugs arranged substantially in a plane on said humidifier heater with adjacent ends of said lugs defining spaces therebetween; a humidifier element having a surface for heating and a coacting holding means for removably holding said heating surface and said surfaces for heating in heating disposition relative to each other, said coacting holding means being selected from, (a) direct coacting holding means comprising circumferentially spaced coacting lugs lying substantially in a plane on said humidifier element, adjacent ends of said coacting lugs defining spaces therebetween, the dimensions and positioning of coacting lugs and the spacing therebetween being such that said coacting lugs are in use passed through the spaces between said heater lugs and then rotated to a position in which said heater lugs and coacting lugs engage each other to maintain said surface for heating in said heating disposition with heater surface and, (b) an indirect holding means comprising (1) an intermediate adaptor comprising a ring member carrying circumferentially spaced adapting coacting lugs lying substantially in a plane on said member, adjacent ends of said adapting coacting lugs defining spaces therebetween, the dimensions and positioning of said heater lugs and said adapting coacting lugs being such that said adapting coacting lugs are in use passed through the spaces between said heater lugs and then rotated to a holding position and (2) humidifier element holding means secured to said ring and adapted to be slidably connected with the humidifier element whereby with said intermediate adaptor in position, said humidifier element is removably maintained with said heating surface and said surface for heating in said heating disposition relative to each other.

To those skilled in the art to which this invention relates, many changes in construction and widely differing embodiments and applications of the invention will suggest themselves without departing from the scope of the invention as defined in the appended claims. The disclosures and the description herein are purely illustrative and are not intended to be in any sense limiting.

Figure 2:
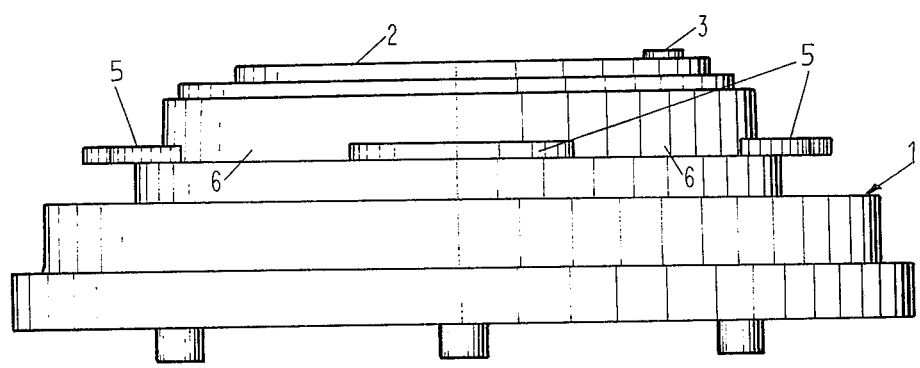
Figure 4:
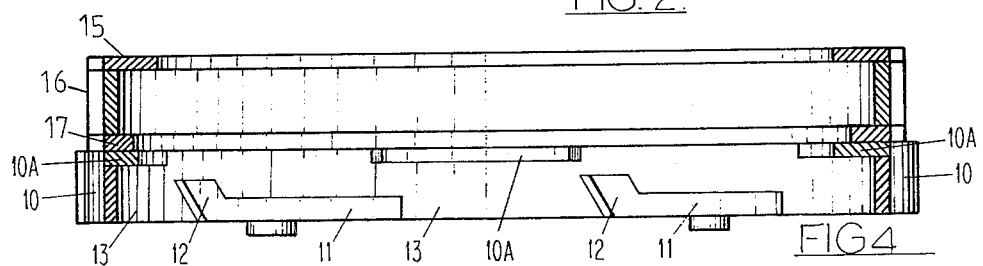
Figure 3:
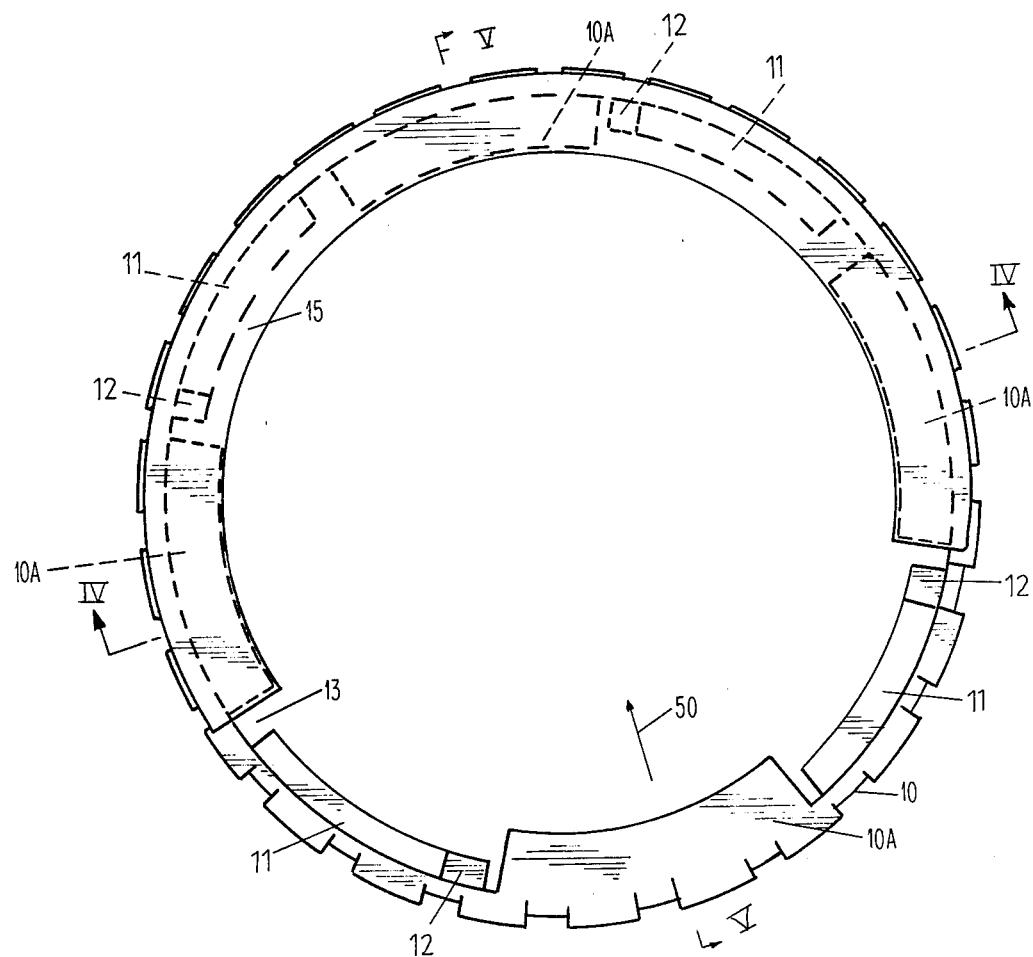
Figure 6:
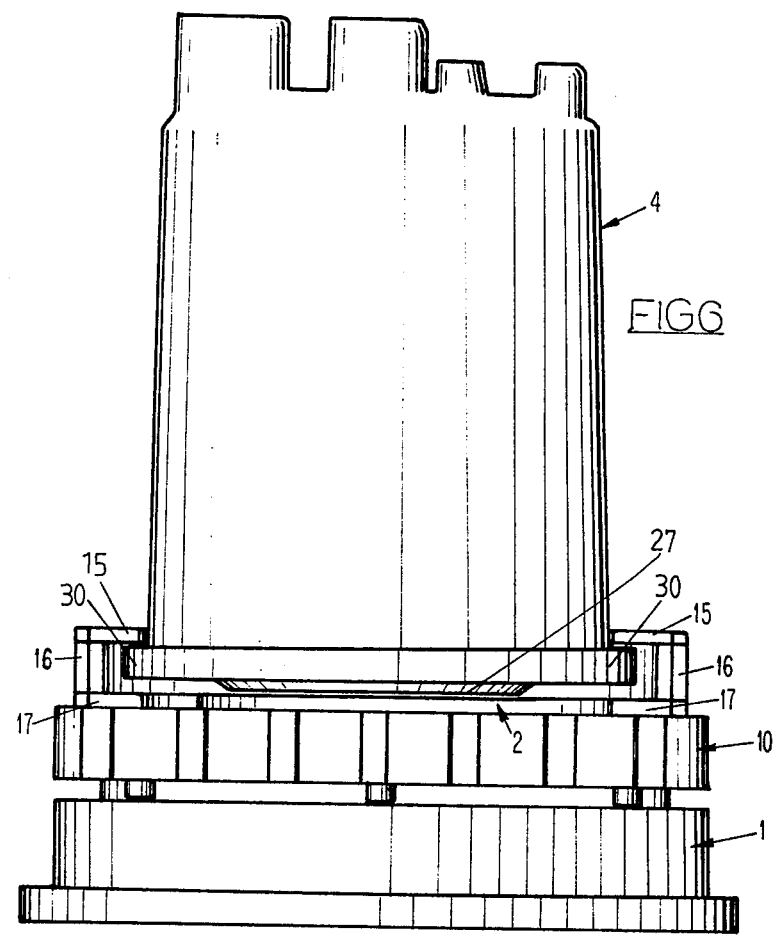
Figure 5:
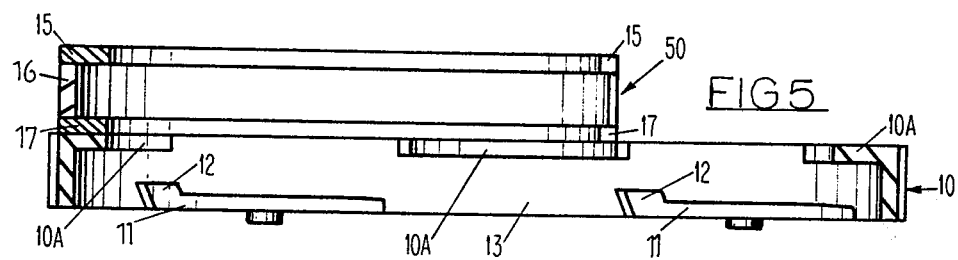
Figure 7:
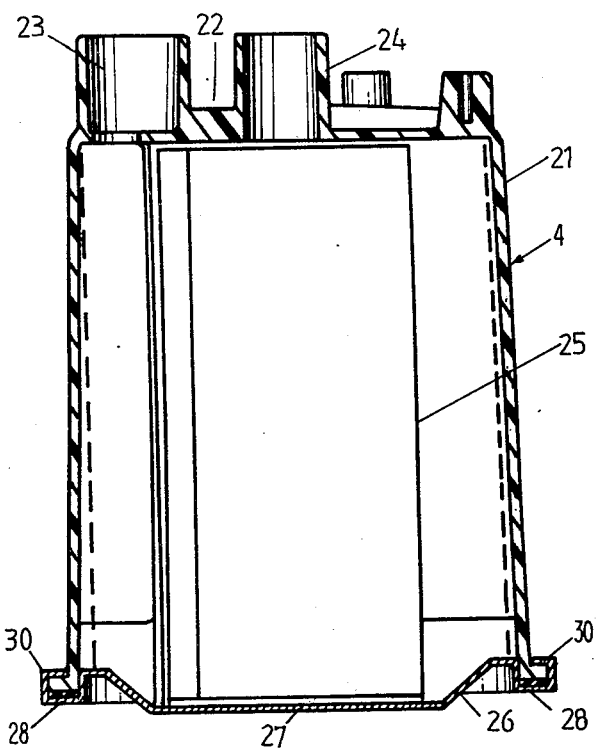
Figure 8:
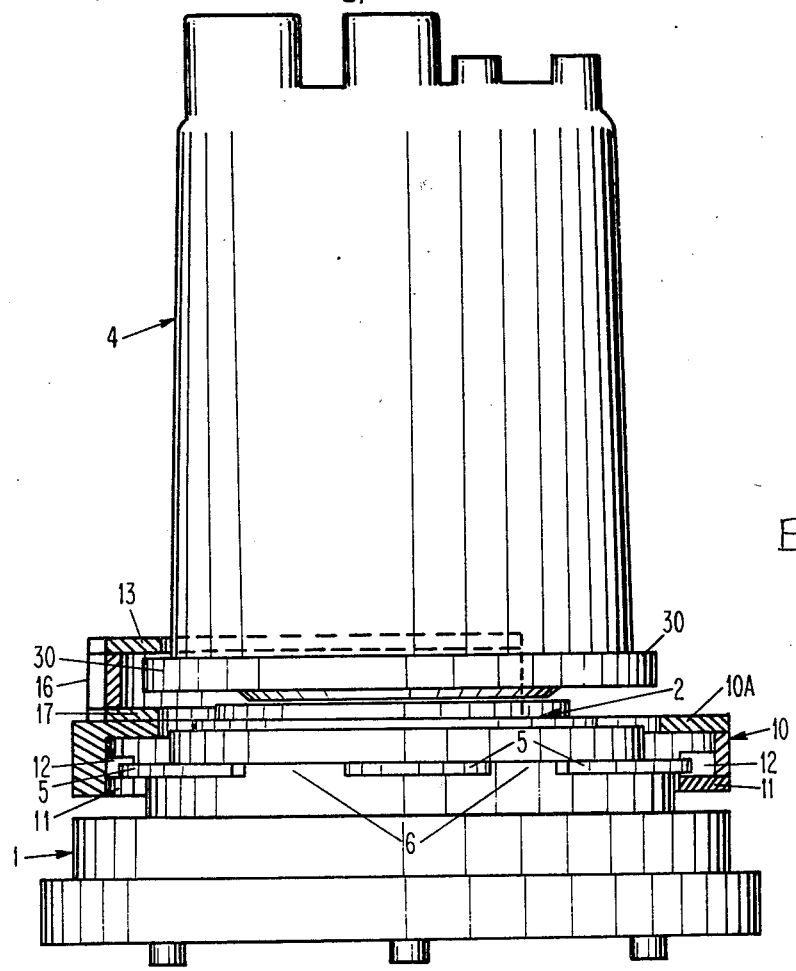

One preferred form of the invention will now be described with reference to the accompanying drawings in which, FIGS. 1 & 2 are, respectively a top plan and a side elevational view of a humidifier heater for use in the invention, FIG. 3 is a top plan view of an intermediate adaptor for use in connecting the humidifier heater of FIGS. 1 & 2 with a humidifier element, FIG. 4 is a cross-sectional view taken on line IV—IV of FIG. 3, FIG. 5 is a cross-section on the line V—V of FIG. 3, FIG. 6 is a side elevation of a humidifying element mounted in position in the adaptor of FIG. 3, the adaptor in turn being mounted on the humidifier heater of FIGS. 1 and 2, FIG. 7 is a cross-section of the humifiying element shown in FIG. 6, and, FIG. 8 is a partial cross-section of an adaptor ring in use with the humidifier heater and humidifier element.

Referring to the drawings the apparatus shown in the drawings is used for the purpose of humidifying gas for inspiration by a patient in, for example, an intensive care section of a hospital and such devices are by now quite well known.

In the contruction shown in the drawings, humidifier heater 1 has mounted within it a spring loaded electric heating plate 2 which carries a temperature sensing device 3 so that the temperature of the base of a humidifying element 4 (FIGS. 6 and 7) which comes into contact with the sensing device 3 can be measured. The humidifier heater 1 carries a plurality of heater lugs 5 spaced around the plate 2, the lugs 5 also having spaces 6 therebetween and being spaced from other parts of the humidifier heater 1.

Referring now to FIGS. 3 to 5, there is shown in these figures an intermediate adaptor constructed as follows:

The intermediate adaptor comprises a ring 10 having in one portion thereof a series of coacting lugs 11 with stops 12 at one end thereof to limit the amount of movement along the lugs 11. The lugs 11 have spaces 13 therebetween which permit the passage between the lugs 11 of the heater lugs 5 so that by placing the ring 10 on the humidifier heater 1 with the lugs 11 aligned with the spaces 6 between the lugs 5 and with the plane of the top of lugs 11 lying below the bottom of the lugs 5 (see FIG. 8) and giving to the ring rotary motion until the stops 12 engage lugs 5, the adaptor is secured in relation to the heater 1.

The ring 10 has an upper surface formed by a plurality of circumferentially spaced inwardly directed flanges 10A.

Mounted on the ring 10 above flanges 10A is a humidifier element holding means comprising a partial annular disc 15 associated with a partial cylindrical spacer 16. These two members are joined to a further partial annular disc 17, the whole being in the form of a horse shoe but with the cross-section of the horse shoe in the form of a channel member as is shown more particularly in FIGS. 4 and 5. The assembly comprising 15, 16 and 17 is fixed to the upper surface ring 10 in any convenient manner, for example, by riveting or it may be made integral therewith.

Referring now to FIGS. 6 and 7, in FIG. 7 there is shown a humidifier element 4 having walls 21, a top 22 carrying an inlet 23 and an outlet 24, the element being fitted with a scroll 25 on which an absorbent material such as blotting paper is fixed and the element being completed by a bottom member 26 having a flat portion 27 which in use engages the heating plate 2 of the humidifier heater 1. The bottom part 26 is of a metal while the walls 21 and top 22 are of a suitable plastic material such as polycarbonate. There is a seal 28 between the walls 21 and the bottom member 26 and a flange or shoulder 30 is provided on an upper part of the junction between the walls and bottom. As will be seen in FIG. 6, the upper surface of flange 30 engages with the under surface of partial annular disc member 15 and the height dimensions of the partial cylindrical spacer 16 are arranged so that when in the position shown in FIG. 6 the flat part 27 is in a heating disposition e.g., in contact with the heating plate 2. It is to be noted that the humidifier element is moved into its engaged position as shown in FIG. 6 by a sideways movement in the direction of the arrow 50 in FIG. 3 through the open end of the horse shoe shaped assembly comprising 15, 16, and 17.

The above construction is such that by use of the intermediate adaptor a slide on "throw away" humidifier element such as that shown at 4 in FIGS. 6 & 7 is quickly and easily placed in position on the humidifier heater before or after being filled with water, for example, through either of the openings 23 or 24, and then put into use by connecting the appropriate tubes to openings 23 and 24. The intermediate adaptor thus provides an indirect holding means comprising firstly the coaction of lugs 11 and 5 and secondly the coaction of flange 30 and partial annular disc 15.

We claim:

1. An intermediate adaptor for connecting a humidifier heater having a heating surface and circumferentially spaced connection lugs arranged substantially in a plane on the heater, with adjacent ends of the connection lugs defining spaces therebetween, to a humidifier element having an annular connection flange, said adaptor comprising a ring and horse-shoe shaped member affixed to the upper surface thereof;

said ring having circumferentially spaced coacting lugs lying substantially in a plane with adjacent ends of said coacting lugs defining spaces therebetween, the dimensions and positioning of said coacting lugs being such that said coacting lugs are capable in use of being passed through the spaces between the connection lugs of the humidifier heater and then rotated to a holding position wherein the coacting lugs engage the connection lugs;

said horse-shoe shaped member comprising a partial annular disc spaced above said ring by a partial hollow cylindrical spacer, said disc and spacer defining a gap dimensioned to slidably receive the connection flange of the humidifier element as the humidifier element is slid to and from a heating contact position by movement of the humidifier element between the legs of the horse-shoe shaped member in a plane parallel to the plane containing said partial disc;

the humidifier element thereby being adapted to be held between the legs of said horse-shoe shaped member in a heating disposition relative to the heating surface by engagement of said partial disc and the connection flange.

2. A humidifier comprising: a humidifier heater having a heating surface and circumferentially spaced connection lugs arranged substantially in a plane on the heater with adjacent ends of the connection lugs defining spaces therebetween;

a humidifier element having an annular connection flange; and an intermediate adaptor securing said humidifier element to said humidifier element, said adaptor comprising a ring and a horse-shoe shaped member affixed to the upper surface thereof;

said ring having circumferentially spaced coacting lugs lying substantially in a plane with adjacent ends of said coacting lugs defining spaces therebetween, the dimensions and positioning of said coacting lugs being such that in use said coacting lugs pass through the spaces between said connection lugs of said humidifier heater and are rotated to a holding position wherein said coacting lugs engage said connection lugs said coacting lugs and connection lugs being engaged to secure the adaptor to the humidifier heater;

said horse-shoe shaped member comprising a partial annular disc spaced above said ring by a partial hollow cylindrical spacer, said disc and spacer defining a gap dimensioned to slidably receive said connection flange of said humidifier element as said humidifier element is slid to and from a heating contact position by movement of said humidifier element between the legs of said horse-shoe shaped member in a plane parallel to the plane containing said partial disc;

said humidifier element being held between the legs of said horse-shoe shaped member in a heating disposition relative to said heating surface by engagement of said partial disc and said connection flange.

* * * * *